(12) United States Patent
Spahr

(10) Patent No.: US 9,717,905 B2
(45) Date of Patent: Aug. 1, 2017

(54) BACKUP SOUND PROCESSOR WITH MULTI-USER FUNCTIONALITY

(71) Applicant: ADVANCED BIONICS AG, Staefa (CH)

(72) Inventor: Anthony J. Spahr, Newbury Park, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/024,021

(22) PCT Filed: Sep. 30, 2013

(86) PCT No.: PCT/US2013/062580
§ 371 (c)(1),
(2) Date: Mar. 22, 2016

(87) PCT Pub. No.: WO2015/047381
PCT Pub. Date: Apr. 2, 2015

(65) Prior Publication Data
US 2016/0243360 A1  Aug. 25, 2016

(51) Int. Cl.
*A61N 1/00* (2006.01)
*A61N 1/36* (2006.01)
*A61N 1/372* (2006.01)

(52) U.S. Cl.
CPC ..... *A61N 1/36032* (2013.01); *A61N 1/37235* (2013.01)

(58) Field of Classification Search
USPC ........................................................ 607/57
See application file for complete search history.

(56) References Cited

U.S. PATENT DOCUMENTS

| 5,800,473 A | 9/1998 | Faisandier |
|---|---|---|
| 7,502,653 B2 | 3/2009 | Daly |

(Continued)

FOREIGN PATENT DOCUMENTS

| WO | WO-03/003956 | 1/2003 |
|---|---|---|
| WO | WO-03/009207 | 1/2003 |

(Continued)

OTHER PUBLICATIONS

International Search Report and Written Opinion received in International Application No. PCT/US2013/062580, dated Mar. 19, 2014.

*Primary Examiner* — Nicole F Johnson
(74) *Attorney, Agent, or Firm* — ALG Intellectual Property, LLC

(57) ABSTRACT

An exemplary backup sound processor maintains data representative of a first set of sound processing programs associated with a first memory slot and with a plurality of cochlear implants, maintains data representative of a second set of sound processing programs associated with the second memory slot and with the plurality of cochlear implants, and detects a communicative coupling of the sound processor to a cochlear implant included in the plurality of cochlear implants. In response, the backup sound processor 1) determines an identifier unique to the cochlear implant, 2) determines that a program switch associated with the sound processor is in a first program switch position, 3) queries the first set of sound processing programs to identify a sound processing program included in the first set of sound processing programs that is associated with the determined identifier, and 4) operates in accordance with the identified sound processing program.

20 Claims, 15 Drawing Sheets

(56) References Cited

U.S. PATENT DOCUMENTS

| | | |
|---|---|---|
| 8,818,517 B2 | 8/2014 | Faltys et al. |
| 2004/0176822 A1 | 9/2004 | Thompson et al. |
| 2008/0267434 A1 | 10/2008 | Schumaier |
| 2009/0222064 A1 | 9/2009 | Faltys et al. |
| 2009/0306742 A1 | 12/2009 | Van Dijk et al. |
| 2012/0029593 A1 | 2/2012 | Calle et al. |
| 2012/0029595 A1* | 2/2012 | Kruger ............... A61N 1/36032 607/57 |
| 2012/0116480 A1* | 5/2012 | Tsay .................. A61N 1/36032 607/57 |

FOREIGN PATENT DOCUMENTS

| | | |
|---|---|---|
| WO | WO-2007/090243 | 8/2007 |
| WO | WO-2012/016007 | 2/2012 |
| WO | WO-2012/016011 | 2/2012 |
| WO | WO-2012/082125 | 6/2012 |

* cited by examiner

BACKUP SOUND PROCESSOR WITH MULTI-USER FUNCTIONALITY

BACKGROUND INFORMATION

Cochlear implant users rely on the uptime and availability of their cochlear implant system hardware in order to maintain their sense of hearing. However, the reliability of a user's external cochlear implant system hardware, such as a sound processor, may be limited. For example, a sound processor may be subject to damage, theft, or loss. As a result, it may be desirable for a cochlear implant user to keep a backup sound processor that can be used in place of his or her primary sound processor in the event that the primary sound processor becomes inoperable or otherwise unavailable. However, doing so can be prohibitively costly, inconvenient, and/or impractical for many cochlear implant users.

For example, some centers (e.g. schools) serve a significant population of cochlear implant users, each of whom may, at times, benefit from the use of a backup sound processor. However, because the use of a backup processor is intermittent for any given user, maintaining a separate backup processor for each user is an inefficient use of resources. Hence, it would be desirable for such a center to maintain a common backup sound processor that may be shared among all of the users at the center. Unfortunately, because sound processors are conventionally programmed for only one user, personnel at the center would have to reprogram the backup sound processor each time it is to be used with a different user. This requires specialized programming hardware, time, and expertise, thus making it difficult for a single backup sound processor to be effectively shared between multiple users.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
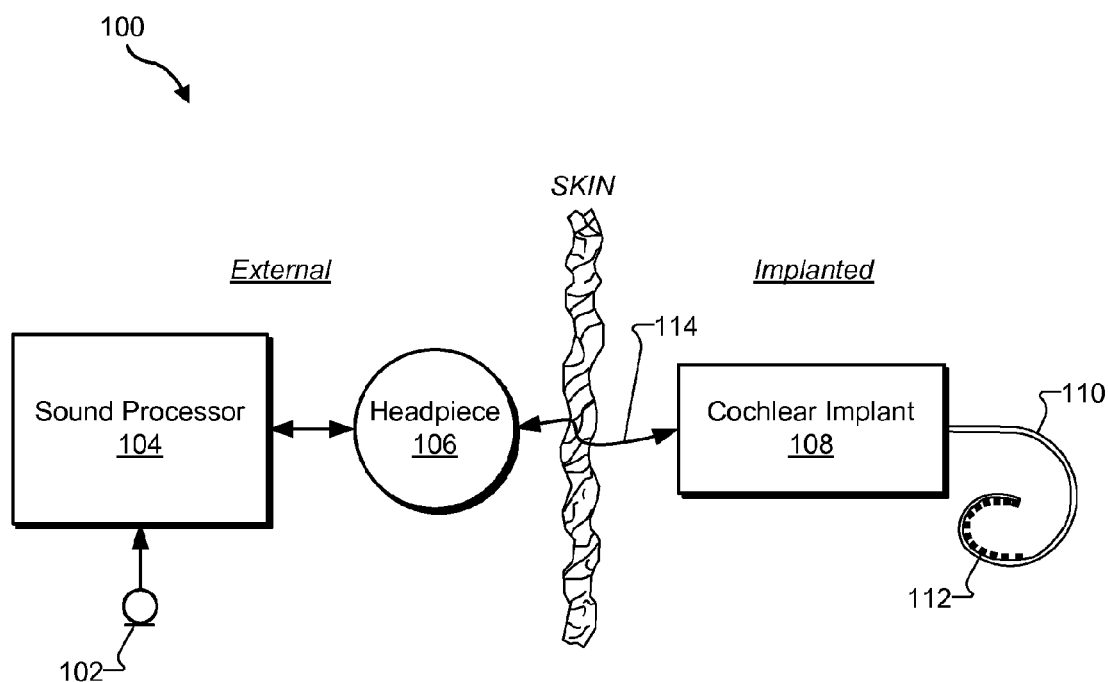
FIG. 1 illustrates an exemplary cochlear implant system according to principles described herein.

A backup sound processor with multi-user functionality is described herein. As will be described below, the backup sound processor (also referred to herein as simply a "sound processor") may be easily and readily swapped between a plurality of cochlear implant users (e.g., a group of cochlear implant users in a school, clinic, or household) without having to manually reprogram the backup sound processor each time a different cochlear implant user desires to use it in place of his or her primary sound processor.

To illustrate, each cochlear implant user (or simply "user") included in a plurality of users may be fitted with a particular sound processor (referred to herein as a "primary sound processor"). Each primary sound processor may have a set of sound processing programs loaded thereon. For example, each sound processor may have a first sound processing program loaded onto a first memory slot and a second sound processing program loaded onto a second memory slot. A user may direct a sound processor to switch between operating in accordance with the first and second sound processing programs by interacting with a program switch (e.g., a program switch disposed on the surface of the sound processor). For example, the user may direct the sound processor to operate in accordance with the first sound processing program by moving the program switch to a first program switch position. Likewise, the user may direct the sound processor to operate in accordance with the second sound processing program by moving the program switch to a second program switch position.

Each set of sound processing programs maintained by each sound processor associated with the plurality of users may be customized to a particular user (i.e., to a particular cochlear implant associated with a user). Because of this, it may be undesirable (and, in some cases, unsafe) for a particular cochlear implant user to use another cochlear implant user's sound processor. Hence, each set of sound processing programs may be linked to (i.e., may only work with) a particular cochlear implant associated with a particular user. In this manner, a sound processor that has sound processing programs linked to a cochlear implant associated with a particular user will not work if paired with a cochlear implant associated with a different user.

In accordance with the systems and methods described herein, a single backup sound processor may be provided to serve the backup needs of each user included in a plurality of users by loading each set of sound processing programs associated with each user onto the backup sound processor. In this configuration, the backup sound processor may be paired with a cochlear implant associated with any of the users, detect an identifier unique to the cochlear implant, and use the identifier to operate in accordance with a set of sound processing programs corresponding to the cochlear implant.

To illustrate, reference is again made to the example described above where each user included in the plurality of users is fitted with a primary sound processor that maintains a first sound processing program in a first memory slot corresponding to a first program switch position and a second sound processing program in a second memory slot corresponding to a second program switch position. In accordance with the systems and methods described herein, the backup sound processor may maintain, within a first memory slot corresponding to the first program switch position, data representative of a first set of sound processing programs associated with the first memory slot and with a plurality of cochlear implants implanted within a plurality of users. In other words, the backup sound processor may store, within the backup sound processor's first memory slot, data representative of each sound processing program that is loaded onto the first memory slot of each primary sound processor used by each user included in the plurality of users. Likewise, the backup sound processor may maintain, within a second memory slot corresponding to the second program switch position, data representative of a second set of sound processing programs associated with the second memory slot and with the plurality of cochlear implants implanted within the plurality of users. In other words, the backup sound processor may store, within the backup sound processor's second memory slot, data representative of each sound processing program that is loaded onto the second memory slot of each primary sound processor used by each user included in the plurality of users.

By maintaining sound processing programs associated with each user within each memory slot, the backup sound processor may replicate any of the primary sound processors used by any of the users included in the plurality of users. For example, the backup sound processor may be communicatively coupled to a cochlear implant included in the plurality of cochlear implants (e.g., by being brought into relatively close proximity of the cochlear implant) while the backup sound processor's program switch is in the first program switch position when. In response, the backup sound processor may 1) determine an identifier unique to the cochlear implant, 2) determine that the program switch is in the first program switch position, 3) query, in accordance with the determination that the program switch is in the first program switch position, the first set of sound processing programs maintained in the first memory slot to identify a sound processing program included in the first set of sound processing programs that is associated with the determined identifier, and 4) operate in accordance with the identified sound processing program. This process may be repeated in response to the backup sound processor being communicatively coupled to any of the other cochlear implants included in the plurality of cochlear implants.

To facilitate an understanding of the systems and methods described herein, an exemplary cochlear implant system 100 will be described in connection with FIG. 1. As shown in FIG. 1, cochlear implant system 100 may include various components configured to be located external to a user including, but not limited to, a microphone 102, a sound processor 104, and a headpiece 106. Cochlear implant system 100 may further include various components configured to be implanted within the user including, but not limited to, a cochlear implant 108 and a lead 110 (also referred to as an electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the user. Microphone 102 may be implemented in any suitable manner. For example, microphone 102 may include a "T-Mic" or the like that is configured to be placed within the concha of the ear near the entrance to the ear canal. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the user. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing program to generate appropriate stimulation parameters for controlling cochlear implant 108. Sound processor 104 may include or be implemented by a behind-the-ear ("BTE") unit, a body worn device, and/or any other sound processing unit as may serve a particular implementation.

Figure 2:
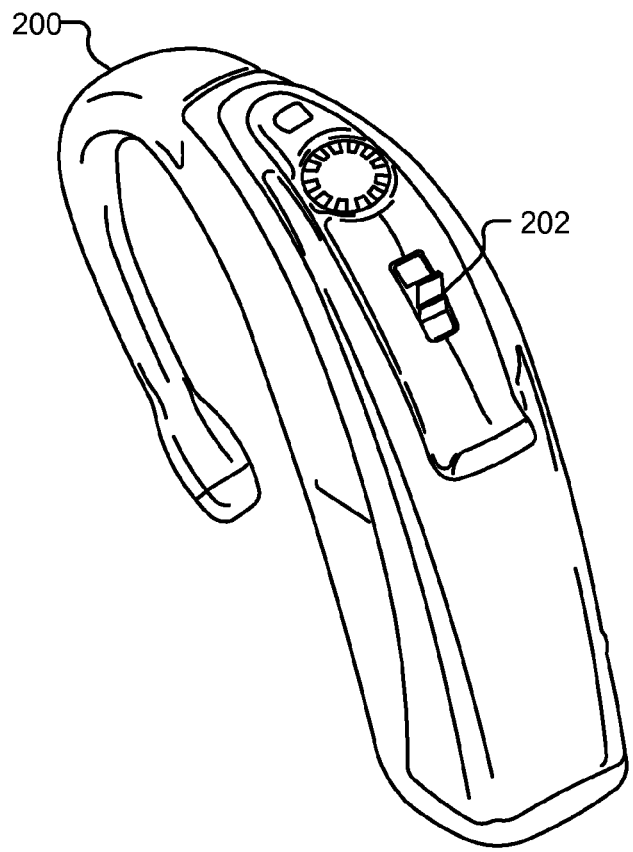
FIG. 2 illustrates an exemplary implementation of a sound processor according to principles described herein.

For example, FIG. 2 is an illustration of an exemplary BTE sound processor 200, which may be representative of any of the sound processors described herein. As shown, BTE sound processor 200 may include a program switch 202 at least partially disposed on an outer surface of the BTE sound processor 200. Program switch 202 may be accessed by a user and moved between various program switch positions. For example, program switch 202 may be configured to be selectively positioned at one of three program switch positions. Each program switch position corresponds to a particular memory slot included within BTE sound processor 200. For example, a first program switch position may correspond to a first memory slot of the BTE sound processor 200, a second program switch position may correspond to a second memory slot of the BTE sound processor 200, and a third program switch position may correspond to a third memory slot of the BTE sound processor 200.

It will be recognized that BTE sound processor 200 (and any of the sound processors described herein) may include any number of program switch positions corresponding to any number of memory slots included within BTE sound processor 200 (or any of the sound processors described herein). It will also be recognized that program switch 202 may be separate from a corresponding particular sound processor (e.g., included within a remote control device associated with the sound processor) and that program switch 202 may be implemented in any suitable manner (e.g., in the form of a software switch).

As described above, each memory slot included in a sound processor (e.g., sound processor 104 and/or BTE sound processor 200) may be loaded with a sound processing program. Each sound processing program may be different (i.e., each sound processing program may process audio content presented to the user in a different manner). A user may direct the sound processor to operate in accordance with a desired sound processing program by moving the program switch associated with the sound processor to a desired program switch position.

Returning to FIG. 1, in some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated unidirectional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the user's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a user and configured to apply stimulation to one or more stimulation sites located along an auditory pathway of a user.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the user via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112.

Figure 3:
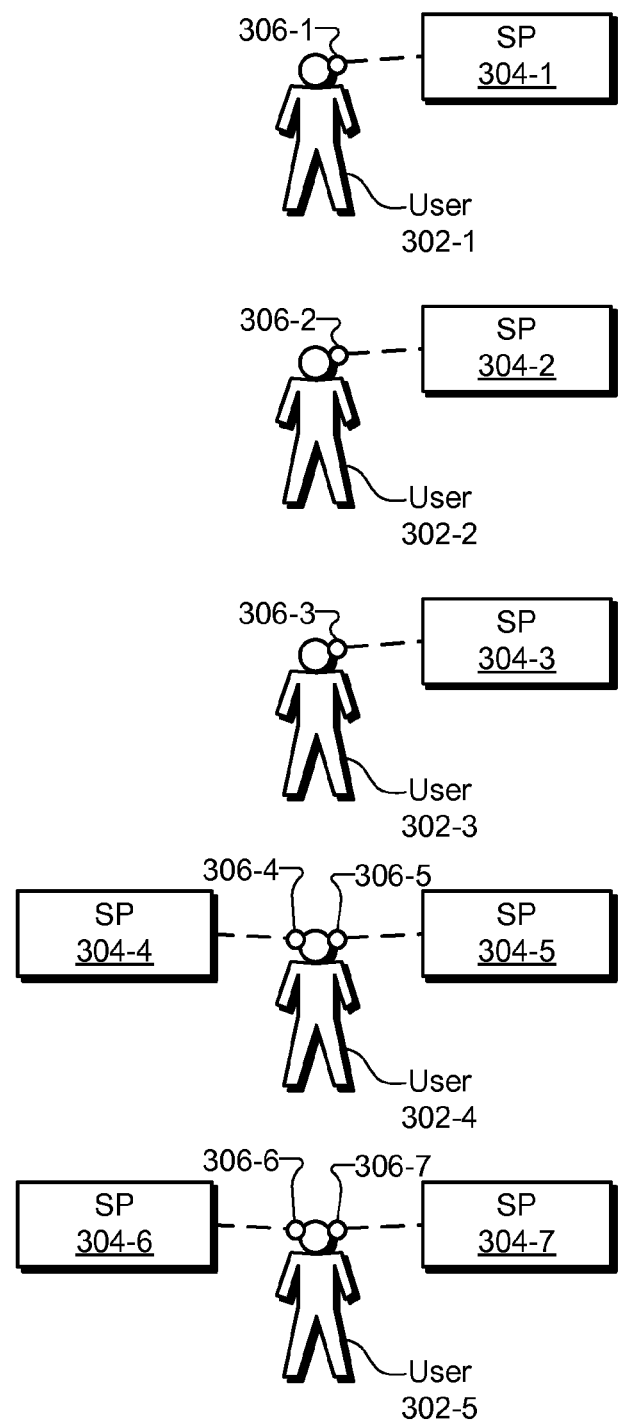
FIGS. 3-5 illustrate the exemplary use of a backup sound processor among a group of cochlear implant users according to principles described herein.

As mentioned, many centers (e.g., schools, clinics, etc.) serve a plurality of cochlear implant users. To illustrate, FIG. 3 shows a plurality of cochlear implant users 302 (e.g., user 302-1 through user 302-5) that may be included in a particular group (e.g., a school class, a group of patients of a clinic, or a household). While five cochlear implant users 302 are shown in FIG. 3, it will be recognized that any other number of cochlear implant users may be included in the plurality of users 302 as may serve a particular implementation.

As shown, each user 302 is fitted with at least one sound processor (e.g., sound processor 304-1 through sound processor 304-7) and at least one cochlear implant 306 (e.g., cochlear implant 306-1 through cochlear implant 306-7). Some users (e.g., users 302-1 through 302-3) may be unilateral cochlear implant users (i.e., fitted with a single sound processor and a single cochlear implant) and some users (e.g., users 302-4 and 302-5) may be bilateral cochlear implant users (i.e., fitted with two sound processors and two cochlear implants—one for each ear).

Each sound processor 304 is communicatively coupled to a particular cochlear implant 306, as illustrated by the dashed lines in FIG. 3. For example, sound processor 304-1 is communicatively coupled to cochlear implant 306-1. In this configuration, each sound processor 304 may govern an operation of its corresponding cochlear implant 306.

In some examples, each cochlear implant 306 has a unique identifier (e.g., a unique serial number). Each cochlear implant 306 may maintain data representative of its unique identifier. In some examples, in order for a particular sound processor 304 to operate in conjunction with a particular cochlear implant 306, the sound processor 304 must have one or more sound processing programs loaded thereon that are associated with (e.g., linked to) the unique identifier of the cochlear implant 306. In this manner, a sound processor (e.g., sound processor 304-1) that has sound processing programs linked to a cochlear implant (e.g., cochlear implant 306-1) associated with a particular user (e.g., user 302-1) will not work if paired with a cochlear implant (e.g., cochlear implant 306-2) associated with a different user (e.g., user 302-2).

At any given time, one of the sound processors 304 associated with users 302 may become inoperable or unavailable. For example, a user 302 may forget to bring his or her sound processor 304 to school. As another example, a sound processor 304 associated with a particular user 302 may run out of battery power and/or become broken. Accordingly, the systems and methods described herein may provide a backup sound processor that may be used in place of any of sound processors 304.

Figure 4:
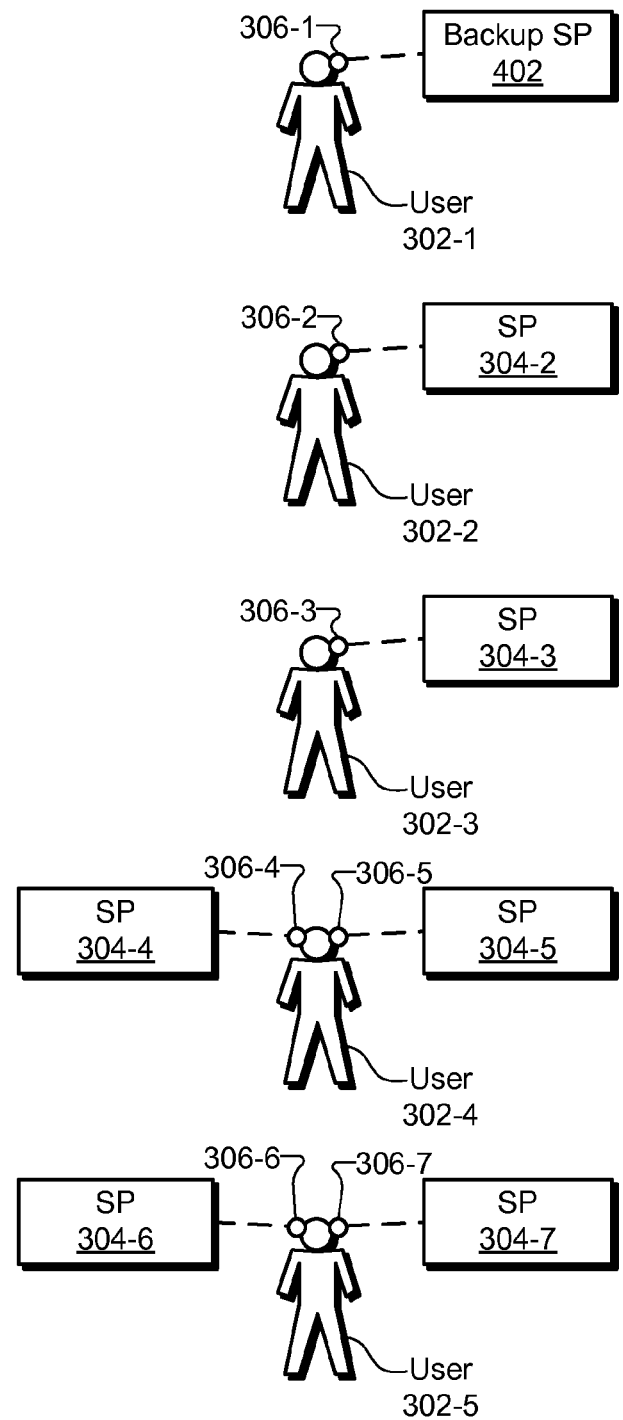

To illustrate, users 302 may be students in a classroom of cochlear implant users. User 302-1 may accidentally forget to bring sound processor 304-1 to class one day. As shown in FIG. 4, a backup sound processor 402 (e.g., a backup sound processor maintained by an instructor of the class) may be provided to user 302-1, who may use backup sound processor 402 in place of sound processor 304-1. In accordance with the systems and methods described herein, backup sound processor 402 may detect that it is communicatively coupled to cochlear implant 306-1 and accordingly provide the same functionality (e.g., operate in accordance with the same sound processing programs) as sound processor 304-1. In this manner, user 302-1 may hear as he or she normally would with sound processor 304-1.

Figure 5:
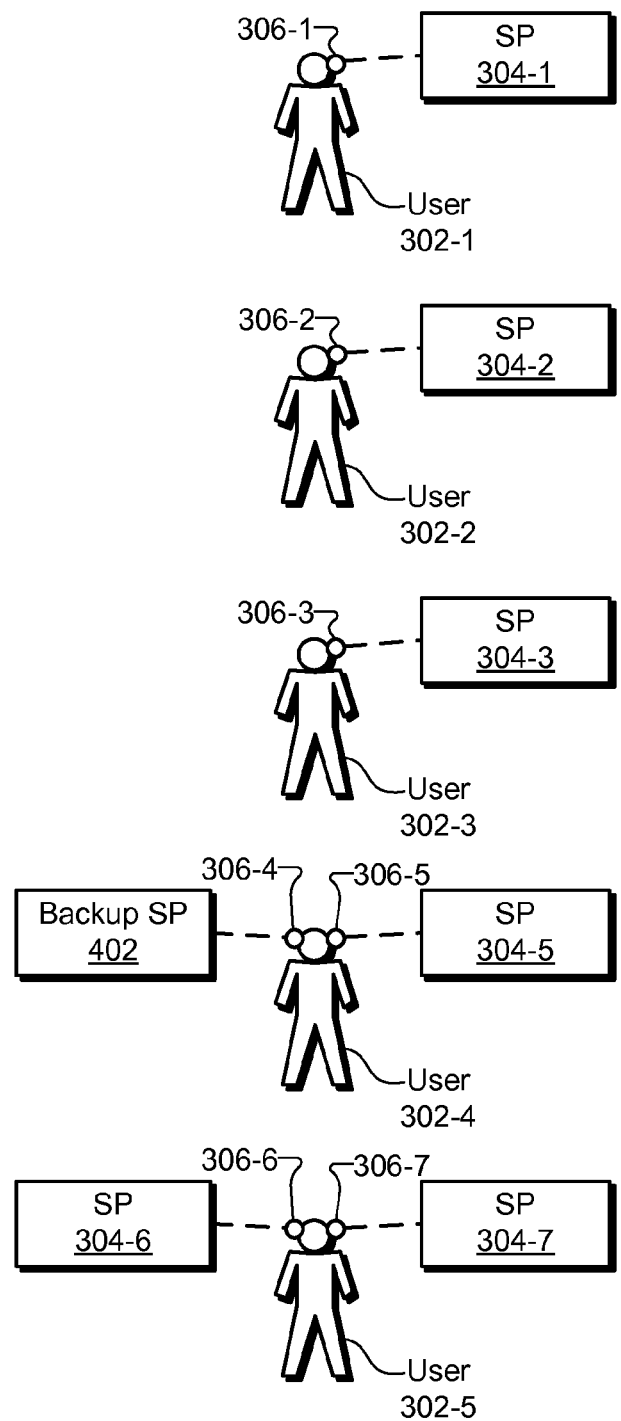

Continuing with this example, sound processor user 304-4 associated with user 302-4 may become inoperable the day after user 302-1 uses backup sound processor 402. FIG. 5 shows that the same backup processor 402 used by user 302-1 may be given to user 302-4, who may use backup sound processor 402 in place of sound processor 304-4. In accordance with the systems and methods described herein, backup sound processor 402 may detect that it is communicatively coupled to cochlear implant 306-4 and accordingly provide the same functionality (e.g., operate in accordance with the same sound processing programs) as sound processor 304-4. In this manner, user 302-4 may hear as he or she normally would with sound processor 304-4.

Figure 6:
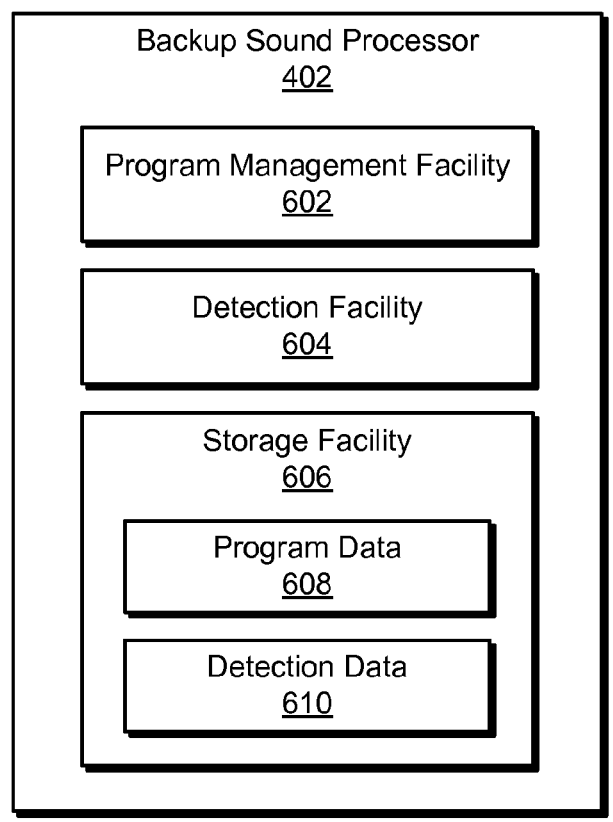
FIG. 6 illustrates exemplary components of a backup sound processor according to principles described herein.

FIG. 6 illustrates exemplary components of backup sound processor 402. It will be recognized that the components shown in FIG. 6 are merely representative of the many different components that may be included in backup sound processor 402 and that backup sound processor 402 may include additional or alternative components as may serve a particular implementation.

As shown in FIG. 6, backup sound processor 402 may include a program management facility 602, a detection facility 604, and a storage facility 606, which may be in communication with one another using any suitable communication technologies. Storage facility 606 may be configured to maintain program data 608 generated and/or used by program management facility 602, and detection data 610 generated and/or used by detection facility 604. Storage facility 606 may maintain additional or alternative data as may serve a particular implementation. One or more of facilities 602-606 may include a computing device or processor configured to perform one or more of the functions described herein.

Program management facility 602 may be configured to maintain data representative of a plurality of different sound processing programs associated with a plurality of different users. For example, each sound processor used by a plurality of users may have three memory slots each loaded with a different sound processing program. In this example, backup processor 402 may also have three memory slots—a first memory slot corresponding to a first program switch position, a second memory slot corresponding to a second program switch position, and a third memory slot corresponding to a third program switch position. Program management facility 602 may maintain, within the first memory slot, data representative of a first set of sound processing programs associated with the first memory slot and with a plurality of cochlear implants (e.g., cochlear implants 306) implanted within the plurality of users. Program management facility 602 may also maintain data representative of a second set of sound processing programs associated with the second memory slot and with the plurality of cochlear implants within the second memory slot and data representative of a third set of sound processing programs associated with the third memory slot and with the plurality of cochlear implants within the third memory slot.

Figure 7:
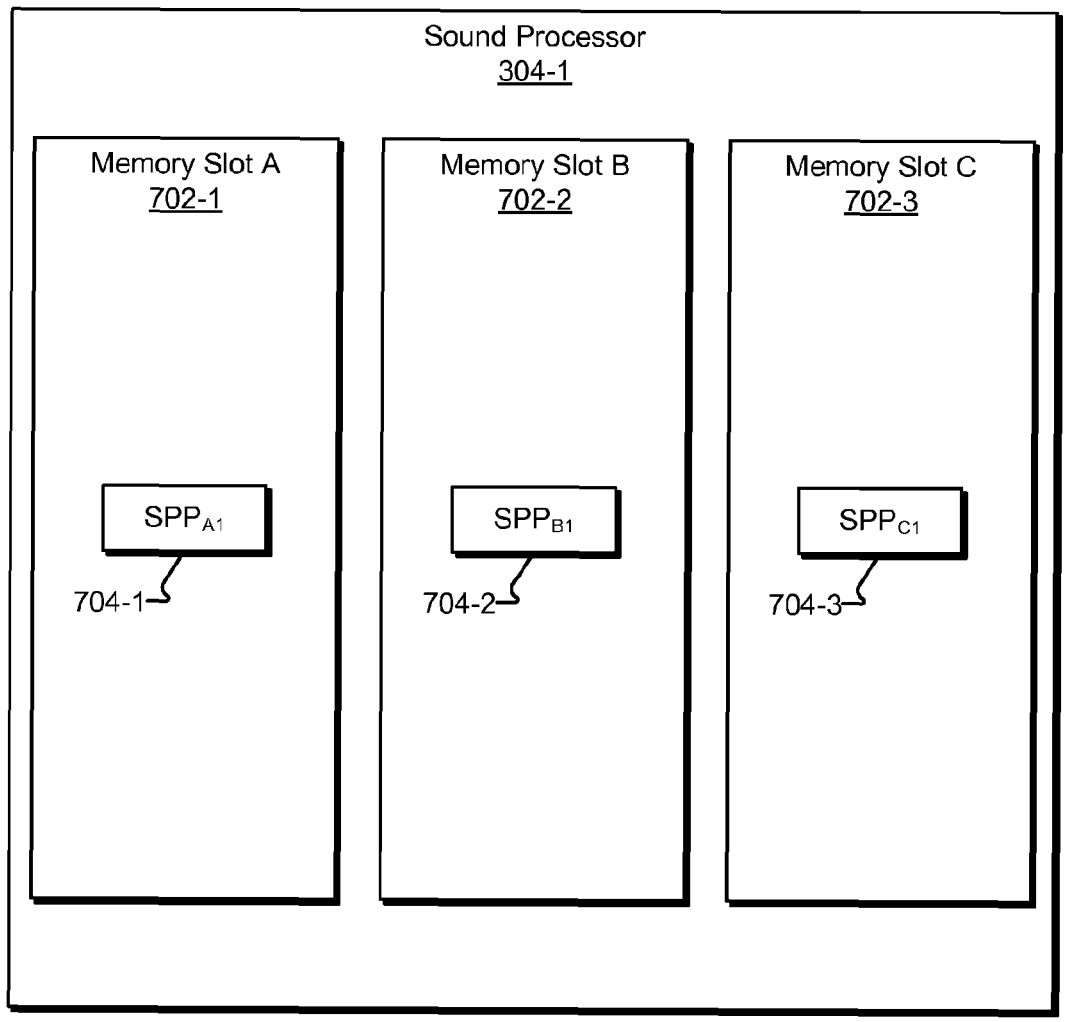
FIG. 7 shows an exemplary implementation of maintaining a sound processing program within each memory slot of a sound processor according to principles described herein.

To illustrate, reference is made to the example provided in FIGS. 3-5 in which backup sound processor 402 is provided for a plurality of users 302 each fitted with one or more sound processors 304 and one or more cochlear implants 306. Each sound processor 304 may have three memory slots each loaded with a different sound processing program. For example, FIG. 7 shows that sound processor 304-1 includes memory slots 702-1 through 702-3 (collectively "memory slots 702"). Memory slot 702-1 is labeled "memory slot A", memory slot 702-2 is labeled "memory slot B", and memory slot 702-3 is labeled "memory slot C".

As shown, a sound processing program 704 is maintained (e.g., loaded) within each memory slot 702. For example, memory slot 702-1 maintains a sound processing program labeled 704-1 and referred to as "$SPP_{A1}$", memory slot 702-2 maintains a sound processing program labeled 704-2 and referred to as "$SPP_{B1}$", and memory slot 702-3 maintains a sound processing program labeled 704-3 and referred to as "$SPP_{C1}$". In the examples provided herein, the subscript "A" indicates that sound processing program 704-1 is associated with the first memory slot 702-1 (i.e., memory slot A), the subscript "B" indicates that sound processing program 704-2 is associated with the second memory slot 702-2 (i.e., memory slot B), and the subscript "C" indicates that sound processing program 704-3 is associated with the third memory slot 702-3 (i.e., memory slot C). As such, sound processor 304-1 may operate in accordance with sound processing program 704-1 if the program switch associated with sound processor 304-1 is in the first program switch position, in accordance with sound processing program 704-2 if the program switch is in the second program switch position, and in accordance with sound processing program 704-3 if the program switch is in the third program switch position.

As indicated by the numerical subscript corresponding to each sound processing program 704 (i.e., the numerical subscript "1"), each sound processing program 704 is also associated with an identifier unique to cochlear implant 306-1. For example, each sound processing program 704 may include data representative of the identifier unique to cochlear implant 306-1. Alternatively, each sound processing program 704 may refer to data representative of the identifier unique to cochlear implant 306-1. For example, program management facility 602 may maintain a look up table or other form of data that associates sound processing programs 704 with the identifier unique to cochlear implant 306-1. It will be recognized that program management facility 602 may associate each sound processing program 704 with the identifier unique to cochlear implant 306-1 in any other manner as may serve a particular implementation. Because each sound processing program 704 is associated with an identifier unique to cochlear implant 306-1, each sound processing program 704 will only work when sound processor 304-1 is communicatively coupled to cochlear implant 306-1.

It will be recognized that the remaining sound processors associated with users 302 (i.e., sound processors 304-2 through 304-7) may similarly maintain distinct sound processing programs within their own memory slots.

Figure 8:
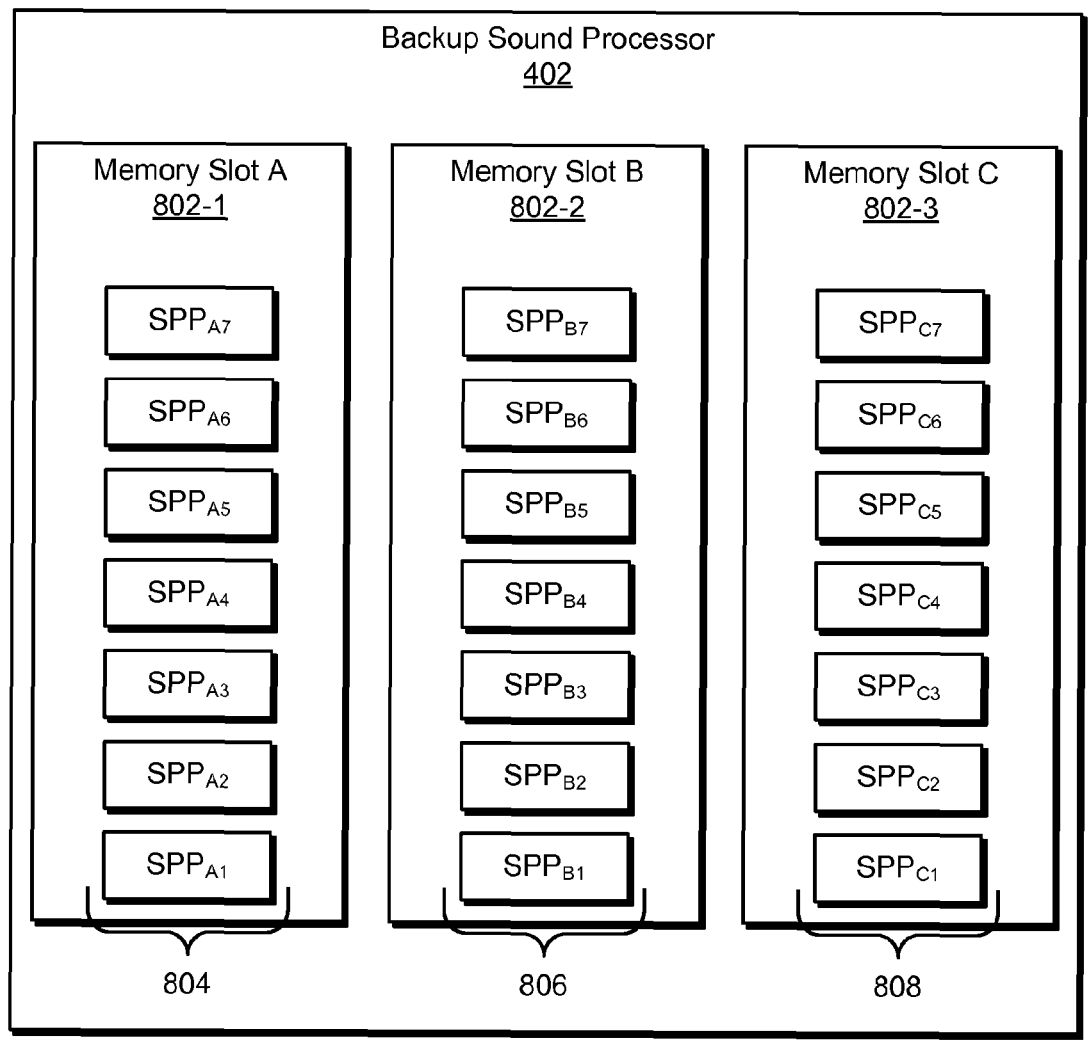
FIG. 8 shows an exemplary implementation of maintaining multiple sound processing programs within each memory slot of a backup sound processor according to principles described herein.

To serve as a backup to any of sound processors 304-1 through 304-7, backup sound processor 402 may maintain data representative of each sound processing program maintained by sound processors 304-1 through 304-7. For example, FIG. 8 shows memory slots 802-1 through 802-3 (collectively "memory slots 802") within backup sound processor 402. Memory slot 802-1 is labeled "memory slot A", memory slot 802-2 is labeled "memory slot B", and memory slot 802-3 is labeled "memory slot C". As shown, backup sound processor 402 may maintain a first set of sound processing programs 804 within memory slot 802-1, a second set of sound processing programs 806 within memory slot 802-2, and a third set of sound processing programs 808 within memory slot 802-3. As shown, the first set of sound processing programs 804 may include each sound processing program maintained within the first memory slot of each sound processor 304 (i.e., sound processing programs $SPP_{A1}$ through $SPP_{A7}$). The second set of sound processing programs 806 may include each sound processing program maintained within the second memory slot of each sound processor 304 (i.e., sound processing programs $SPP_{B1}$ through $SPP_{B7}$). The third set of sound processing programs 808 may include each sound processing program maintained within the third memory slot of each sound processor 304 (i.e., sound processing programs $SPP_{C1}$ through $SPP_{C7}$).

In some examples, backup sound processor 402 (i.e., program management facility 602) may selectively choose which sound processing program included in the different sets of sound processing programs (i.e., sets 804, 806, and 808) in which to operate based on the particular cochlear implant 306 that backup sound processor 402 is paired with and based on the particular position of the program switch associated with backup sound processor 402.

For example, detection facility 604 of backup sound processor 402 may detect a communicative coupling of backup sound processor 402 to a particular cochlear implant (e.g., by detecting an establishment of a wireless communication link between backup sound processor 402 and the cochlear implant). In response to the communicative coupling, program management facility 602 may determine an identifier unique to the cochlear implant, determine that a program switch associated with backup sound processor 402 is in a particular program switch position, and accordingly select a particular sound processing program in which to operate.

Figure 9:
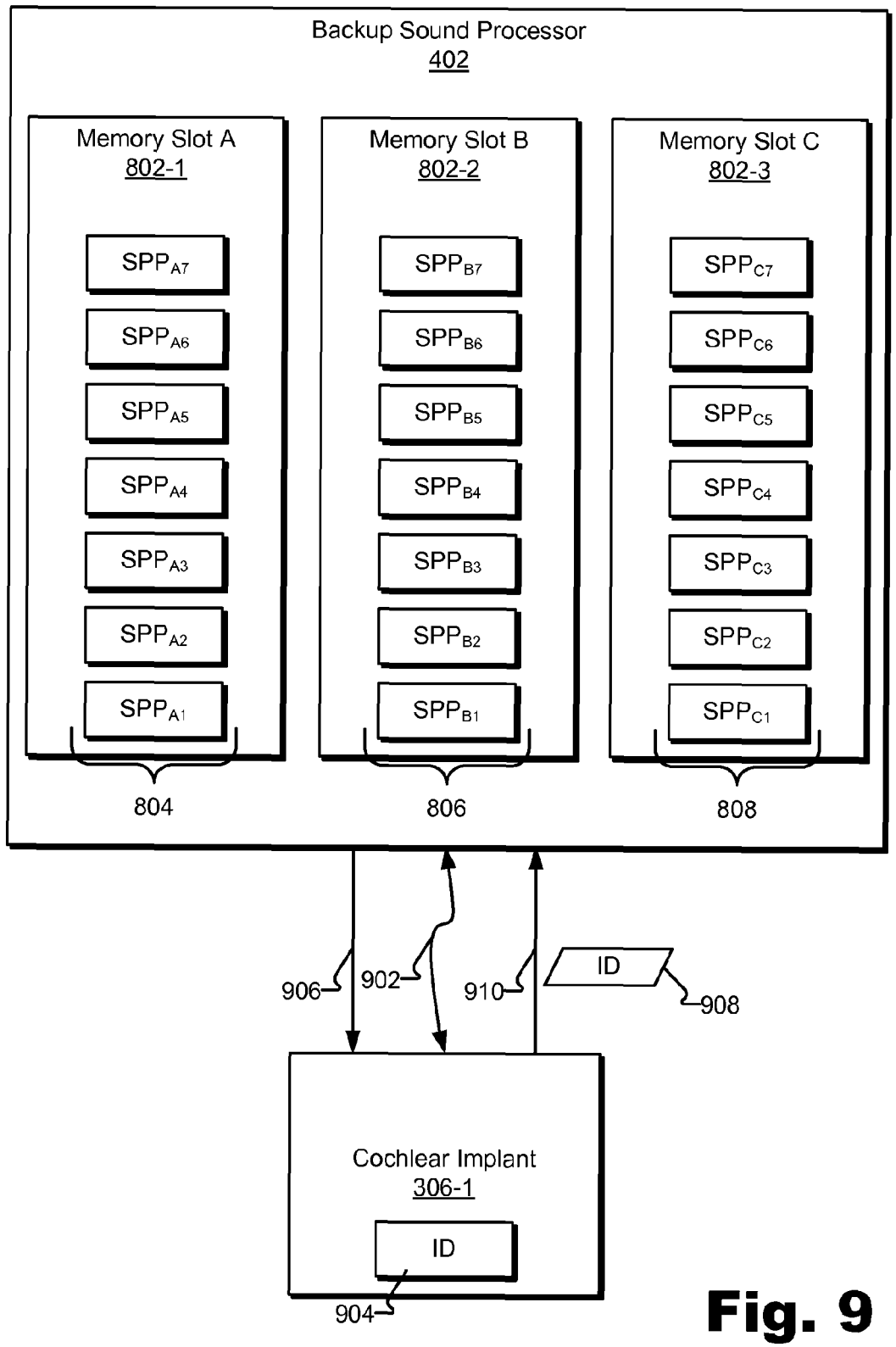
FIG. 9 illustrates an exemplary scenario in which a backup sound processor is communicatively coupled to a cochlear implant according to principles described herein.

To illustrate, FIG. 9 shows an exemplary scenario in which backup sound processor 402 is communicatively coupled to cochlear implant 306-1 by way of a wireless communication link 902. As shown, cochlear implant 306-1 may maintain data representative of an identifier 904 unique to cochlear implant 306-1.

In response to the establishment of wireless communication link 902, program management facility 602 may query cochlear implant 306-1 for identifier 904. This querying is represented by arrow 906 and may be performed in any suitable manner (e.g., by transmitting data to cochlear implant 306-1 requesting that cochlear implant 306-1 provide data representative of the identifier 904).

In response to the query, cochlear implant 306-1 may transmit data 908 representative of the identifier to backup sound processor 402, as represented by arrow 910. Program management facility 602 may receive the data 908 representative of the identifier.

In some examples, program management facility 602 may also determine that a program switch associated with backup sound processor 402 is in the first program switch position (i.e., the position associated with the first memory slot 802-1. Based on this information, program management facility 602 may query the first set of sound processing programs 804 to identify a sound processing program that is associated with identifier 904. In this particular example, because identifier 904 is associated with cochlear implant 306-1, program management facility 602 may identify the sound processing program labeled "$SPP_{A1}$" as being associated with cochlear implant 306-1 and begin operating in accordance with this sound processing program.

Program management facility 602 may operate in accordance with the identified sound processing program in any suitable manner. For example, program management facility 602 may process audio signals presented to the user in accordance with the identified sound processing program.

While operating in accordance with the identified sound processing program (i.e., the sound processing program labeled "$SPP_{A1}$"), the user may move the program switch to another program switch position. For example, the user may move the program switch from the first program switch position to the second program switch position. In response, program management facility 602 may query the second set of sound processing programs 806 to identify a sound processing program that is associated with identifier 904. In this particular example, because identifier 904 is associated with cochlear implant 306-1, program management facility 602 may identify the sound processing program labeled "$SPP_{B1}$" as being associated with cochlear implant 306-1 and begin operating in accordance with this sound processing program.

In some examples, detection facility 604 may detect that backup sound processor 402 is uncoupled from cochlear implant 306-1 and subsequently communicatively coupled to a different cochlear implant. For example, detection facility 604 may detect that backup sound processor 402 communicatively couples to cochlear implant 306-2. In response, program management facility 602 may determine an identifier unique to cochlear implant 306-2 and select a sound processing program (e.g., the sound processing program labeled "$SPP_{A2}$") associated with cochlear implant 306-2 in a similar manner as that described above. Program management facility 602 may then begin operating in accordance with this sound processing program.

Figure 10:
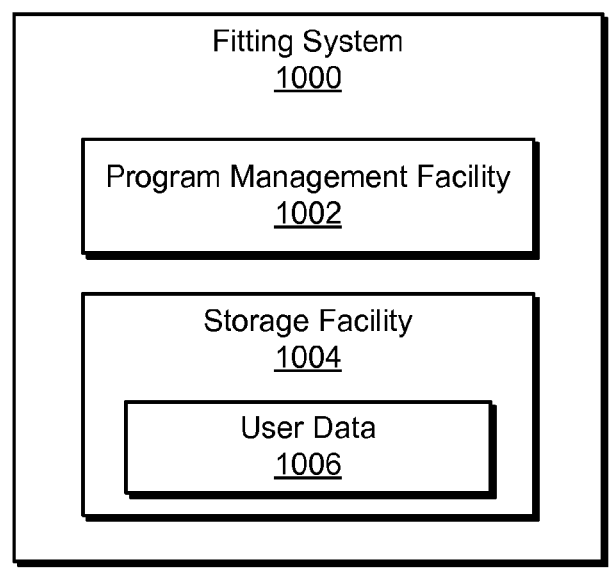
FIG. 10 shows an exemplary fitting system according to principles described herein.

In some examples, program management facility 602 may maintain data representative of a plurality of different sound processing programs associated with a plurality of different users by receiving the data from a fitting system or any other suitable source. For example, FIG. 10 illustrates exemplary components of a fitting system 1000 that may be configured to provide data representative of sound processing programs associated with a plurality of different users to backup sound processor 402 (i.e., to program management facility 602). It will be recognized that the components shown in FIG. 10 are merely representative of the many different components that may be included in fitting system 1000 and that fitting system 1000 may include additional or alternative components as may serve a particular implementation.

As shown in FIG. 10, fitting system 1000 may include a program management facility 1002 and a storage facility 1004, which may be in communication with one another using any suitable communication technologies. Storage facility 1004 may be configured to maintain user data 1006 (e.g., data representative of sound processing programs and/or other information associated with cochlear implant users) generated and/or used by program management facility 1002. Storage facility 1004 may maintain additional or alternative data as may serve a particular implementation.

Fitting system 1000 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation. In some examples, fitting system 1000 may provide one or more graphical user interfaces ("GUIs") (e.g., by presenting the one or more GUIs by way of a display screen) with which a clinician or other user may interact.

Program management facility 1002 may be configured to maintain (e.g., receive and store) data (e.g., user data 1006) associated with a plurality of cochlear implant users directly from a plurality of sound processors associated with the plurality of users. For example, program management facility 1002 may receive data representative of a plurality of sound processing programs associated with a plurality of cochlear implant users directly from a plurality of sound processors associated with the plurality of users.

Figure 11:
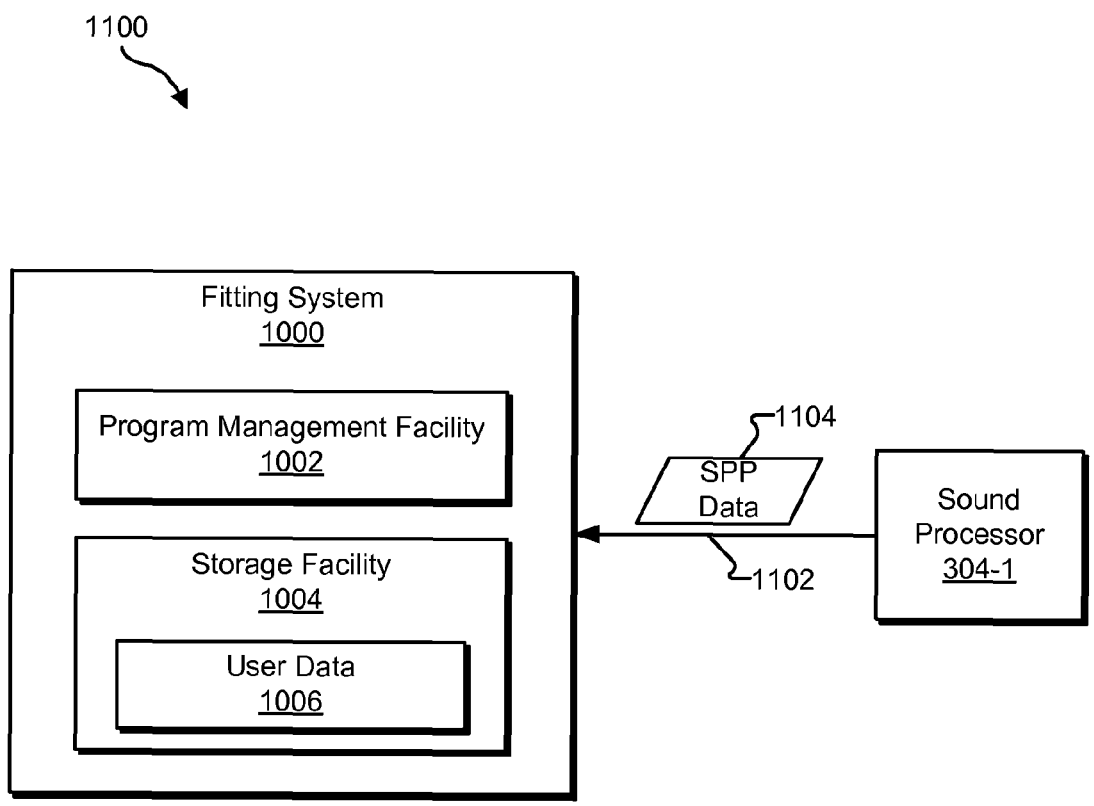
FIG. 11 shows an exemplary configuration in which a sound processor is communicatively coupled to a fitting system according to principles described herein.

To illustrate, FIG. 11 shows an exemplary configuration 1100 in which sound processor 304-1 is communicatively coupled to fitting system 1000. Sound processor 304-1 may be communicatively coupled to fitting system 1000 in any suitable manner. For example, sound processor 304-1 may be selectively coupled to fitting system 1000 by way of a wired link, a wireless link, and/or any other type of link as may serve a particular implementation.

While sound processor 304-1 is communicatively coupled to fitting system 1000, sound processor 304-1 may transmit, as represented by arrow 1102, sound processing program data 1104 (i.e., data representative of one or more sound processing programs maintained by sound processor 304-1) to fitting system 1000. Any suitable communication protocol may be used to transmit sound processing program data 1104 to fitting system 1000. In some examples, sound processing program data 1104 is transmitted automatically in response to a communicative coupling of sound processor 304-1 to fitting system 1000. Alternatively, sound processing program data 1104 is transmitted in response to user input provided by a user (e.g., a clinician) associated with fitting system 1000. It will be recognized that sound processing programs maintained by other sound processors (e.g., sound processors 304-2 through 304-7) may be transmitted to fitting system 1000 in a similar manner.

Fitting system 1000 may be further configured to store data representative of sound processing programs (e.g., sound processing program data 1104) that is received from each sound processor that connects to fitting system 1000. For example, fitting system 1000 may store the sound processing program data in the form of a database.

Figure 12:
FIG. 12 shows an exemplary database that may be maintained by a fitting system according to principles described herein.

FIG. 12 illustrates an exemplary database 1200 that may be maintained by fitting system 1000. As shown in FIG. 12, database 1200 may include data representative of an identifier (e.g., a unique serial number) associated with each of a plurality of cochlear implants that are associated with a plurality of sound processing programs. For example, database 1200 includes seven cochlear implant identifiers (e.g., CI1 through CI7) associated with the seven cochlear implants 306 shown in FIGS. 3-5.

Database 1200 may also include data representative of sound processing programs associated with each cochlear implant identifier. This data may be arranged in a manner that links each sound processing program to a particular memory slot. For example, database 1200 includes data representative of sound processing programs $SPP_{A1}$ through $SPP_{A7}$ in a column associated with the memory slot labeled "memory slot A", data representative of sound processing programs $SPP_{B1}$ through $SPP_{B7}$ in a column associated with the memory slot labeled "memory slot B", and data representative of sound processing programs $SPP_{C1}$ through $SPP_{C7}$ in a column associated with the memory slot labeled "memory slot C". It will be recognized that the exemplary database shown in FIG. 12 is just one example of the many different ways in which fitting system 1000 may maintain sound processing program data.

Program management facility 1002 may be further configured to detect a communicative coupling of backup sound processor 402 to fitting system 1000. While backup sound processor 402 is coupled to fitting system 1000, program management facility 1002 may transmit the stored data representative of each sound processing program to backup sound processor 402.

Figure 13:
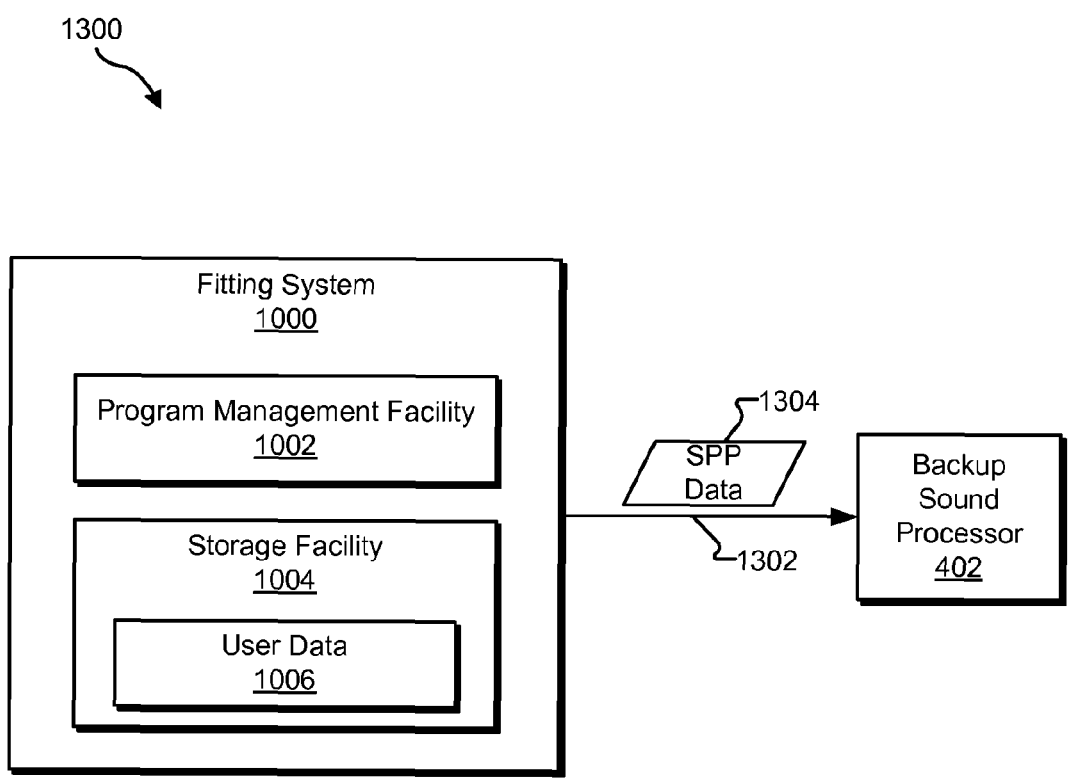
FIG. 13 shows an exemplary configuration in which a backup sound processor is communicatively coupled to a fitting system according to principles described herein.

To illustrate, FIG. 13 shows an exemplary configuration 1300 in which backup sound processor 402 is communicatively coupled to fitting system 1000. Backup sound processor 402 may be communicatively coupled to fitting system 1000 in any suitable manner. For example, backup sound processor 402 may be selectively coupled to fitting system 1000 by way of a wired link, a wireless link, and/or any other type of link as may serve a particular implementation.

In certain examples, program management facility 1002 may detect the communicative coupling of backup sound processor 402 to fitting system 1000, and while communicatively coupled to backup sound processor 402, program management facility 1002 may transmit, as represented by arrow 1302, sound processing program data 1304 to backup sound processor 402.

Figure 14:
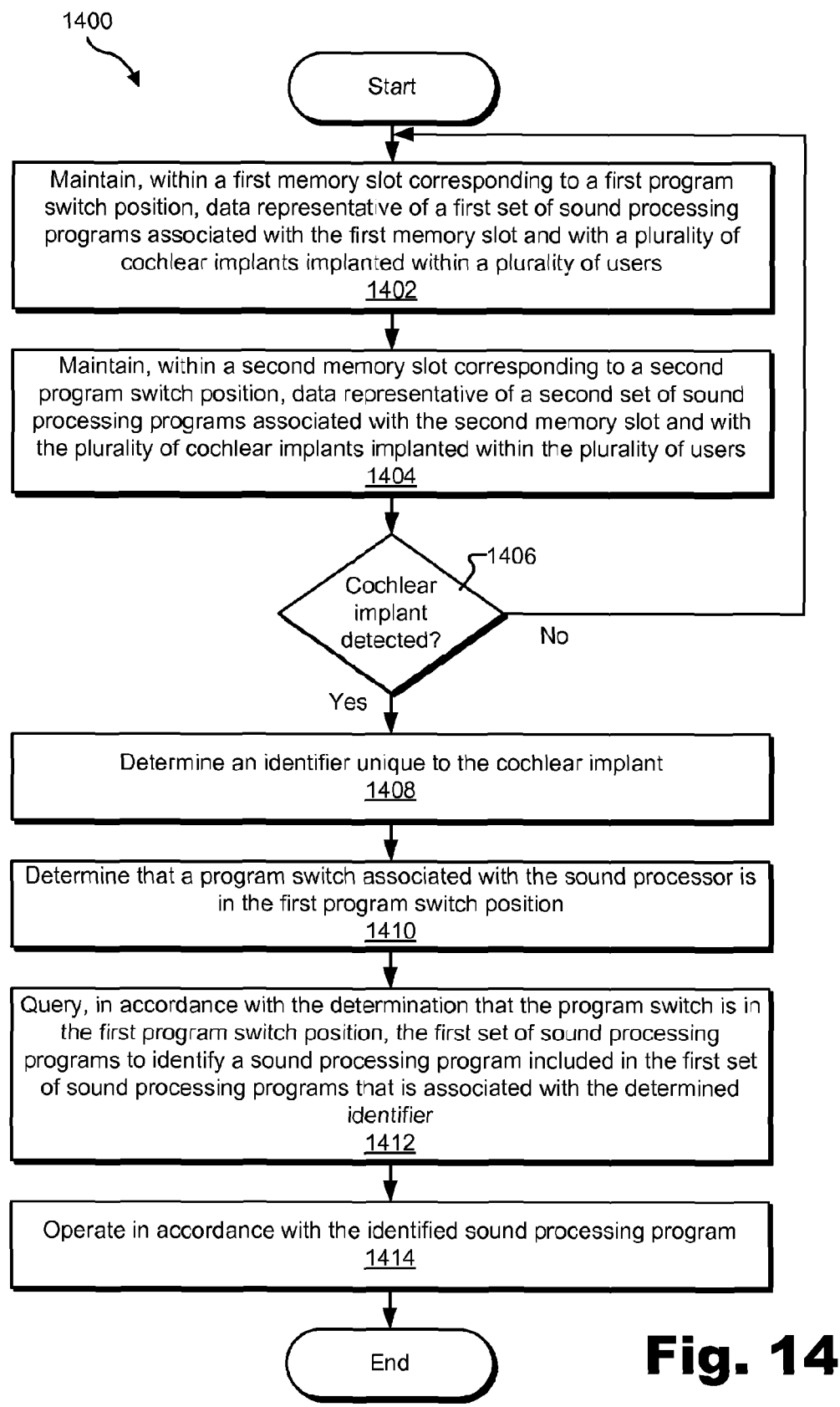
FIG. 14 illustrates an exemplary method according to principles described herein.

FIG. 14 illustrates an exemplary method 1400. While FIG. 14 illustrates exemplary steps according to one embodiment, other embodiments may omit, add to, reorder, and/or modify any of the steps shown in FIG. 14. One or more of the steps shown in FIG. 14 may be performed by backup sound processor 402.

In step 1402, a sound processor maintains, within a first memory slot corresponding to a first program switch position, data representative of a first set of sound processing programs associated with the first memory slot and with a plurality of cochlear implants implanted within a plurality of users. Step 1402 may be performed in any of the ways described herein.

In step 1404, the sound processor maintains, within a second memory slot corresponding to a second program switch position, data representative of a second set of sound processing programs associated with the second memory slot and with the plurality of cochlear implants implanted within the plurality of users. Step 1404 may be performed in any of the ways described herein.

At decision block 1406, the sound processor detects whether the sound processor is communicatively coupled to a cochlear implant included in the plurality of implants. This may be performed in any suitable manner.

If the sound processor does not detect the cochlear implant (No; decision block 1406), the sound processor does not take any additional action. However, if the sound processor detects the cochlear implant (Yes; decision block 1406), the sound processor performs steps 1408 through 1414.

In step 1408, the sound processor determines an identifier unique to the cochlear implant. Step 1408 may be performed in any of the ways described herein.

In step 1410, the sound processor determines that a program switch associated with the sound processor is in the first program switch position. Step 1410 may be performed in any of the ways described herein.

In step 1412, the sound processor queries, in accordance with the determination that the program switch is in the first program switch position, the first set of sound processing programs to identify a sound processing program included in the first set of sound processing programs that is associated with the determined identifier, as described herein. Step 1412 may be performed in any of the ways described herein.

In step 1414, the sound processor operates in accordance with the identified sound processing program. Step 1414 may be performed in any of the ways described herein.

In certain embodiments, one or more of the components and/or processes described herein may be implemented and/or performed by one or more appropriately configured computing devices. To this end, one or more of the systems and/or components described above may include or be implemented by any computer hardware and/or computer-implemented instructions (e.g., software) embodied on a non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known non-transitory computer-readable media.

A non-transitory computer-readable medium (also referred to as a processor-readable medium) includes any non-transitory medium that participates in providing data (e.g., instructions) that may be read by a computer (e.g., by a processor of a computer). Such a non-transitory medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of non-transitory computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other non-transitory medium from which a computer can read.

Figure 15:
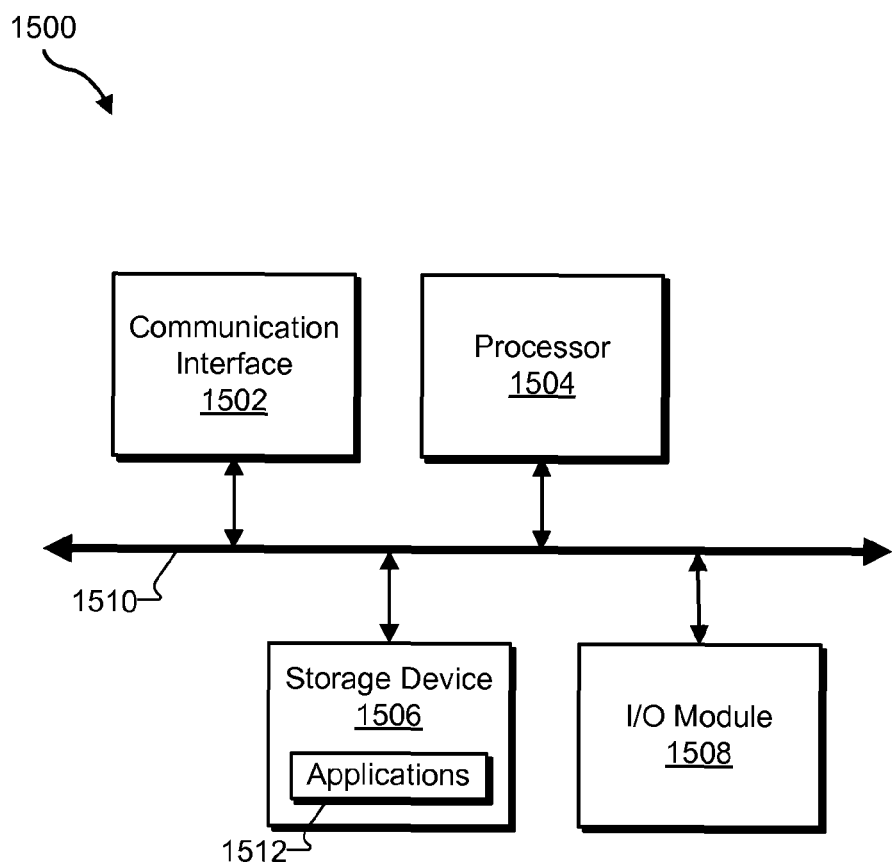
FIG. 15 illustrates an exemplary computing device according to principles described herein.

FIG. 15 illustrates an exemplary computing device 1500 that may be configured to perform one or more of the processes described herein. As shown in FIG. 15, computing device 1500 may include a communication interface 1502, a processor 1504, a storage device 1506, and an input/output ("I/O") module 1508 communicatively connected via a communication infrastructure 1510. While an exemplary computing device 1500 is shown in FIG. 15, the components illustrated in FIG. 15 are not intended to be limiting. Additional or alternative components may be used in other embodiments. Components of computing device 1500 shown in FIG. 15 will now be described in additional detail.

Communication interface 1502 may be configured to communicate with one or more computing devices. Examples of communication interface 1502 include, without limitation, a wired network interface (such as a network interface card), a wireless network interface (such as a wireless network interface card), a modem, and any other suitable interface. Communication interface 1502 may additionally or alternatively provide such a connection through, for example, a local area network (such as an Ethernet network), a personal area network, a telephone or cable network, a satellite data connection, a dedicated URL, or any other suitable connection. Communication interface 1502 may be configured to interface with any suitable communication media, protocols, and formats, including any of those mentioned above.

Processor 1504 generally represents any type or form of processing unit capable of processing data or interpreting, executing, and/or directing execution of one or more of the instructions, processes, and/or operations described herein. Processor 1504 may direct execution of operations in accordance with one or more applications 1512 or other computer-executable instructions such as may be stored in storage device 1506 or another non-transitory computer-readable medium.

Storage device 1506 may include one or more data storage media, devices, or configurations and may employ any type, form, and combination of data storage media and/or device. For example, storage device 1506 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1506. For example, data representative of one or more executable applications 1512 (which may include, but are not limited to, one or more of the software applications described herein) configured to direct processor 1504 to perform any of the operations described herein may be stored within storage device 1506. In some examples, data may be arranged in one or more databases residing within storage device 1506.

I/O module 1508 may be configured to receive user input and provide user output and may include any hardware, firmware, software, or combination thereof supportive of input and output capabilities. For example, I/O module 1508 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1508 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1508 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1500. For example, one or more applications 1512 residing within storage device 1506 may be configured to direct processor 1504 to perform one or more processes or functions associated with program management facility 602, detection facility 604, and/or program management facility 1002. Likewise, storage facility 606 and/or storage facility 1004 may be implemented by or within storage device 1506.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:
1. A sound processor comprising:
    a program management facility that
        maintains, within a first memory slot corresponding to a first program switch position, data representative of a first set of sound processing programs associated with the first memory slot and with a plurality of cochlear implants implanted within a plurality of users, and maintains, within a second memory slot corresponding to a second program switch position, data representative of a second set of sound processing programs associated with the second memory slot and with the plurality of cochlear implants implanted within the plurality of users; and a detection facility communicatively coupled to the program management facility and that detects a communicative coupling of the sound processor to a cochlear implant included in the plurality of cochlear implants, and wherein, in response to the communicative coupling, the program management facility determines an identifier unique to the cochlear implant, determines that a program switch associated with the sound processor is in the first program switch position, queries, in accordance with the determination that the program switch is in the first program switch position, the first set of sound processing programs to identify a sound processing program included in the first set of sound processing programs that is associated with the determined identifier, and operates in accordance with the identified sound processing program.

2. The sound processor of claim 1, wherein the program management facility further maintains, within a third memory slot corresponding to a third program switch position, data representative of a third set of sound processing programs associated with the third memory slot and with the plurality of cochlear implants implanted within the plurality of users.

3. The sound processor of claim 1, wherein the program management facility maintains the data representative of the first set of sound processing programs and the data representative of the second set of sound processing programs by receiving the data representative of the first set of sound processing programs and the data representative of the second set of sound processing programs from a fitting system communicatively coupled to the sound processor.

4. The sound processor of claim 1, wherein the program management facility further:

determines that the program switch switches to being in the second program switch position;

queries, in response to the program switch switching to being in the second program switch position, the second set of sound processing programs to identify a sound processing program included in the second set of sound processing programs that is associated with the determined identifier; and operates in accordance with the identified sound processing program included in the second set of sound processing programs.

5. The sound processor of claim 1, wherein:

the detection facility detects that the sound processor is uncoupled from the cochlear implant and communicatively couples to an additional cochlear implant included in the plurality of cochlear implants; and wherein, in response to the communicative coupling to the additional cochlear implant, the program management facility determines an additional identifier unique to the additional cochlear implant, determines that the program switch associated with the sound processor is in the first program switch position, queries, in accordance with the determination that the program switch is in the first program switch position, the first set of sound processing programs to identify an additional sound processing program included in the first set of sound processing programs that is associated with the determined additional identifier, and operates in accordance with the identified additional sound processing program.

6. The sound processor of claim 5, wherein:

the cochlear implant is associated with a first ear of a user included in the plurality of users; and the additional cochlear implant is associated with a second ear of the user included in the plurality of users.

7. The sound processor of claim 5, wherein:

the cochlear implant is implanted within a first user included in the plurality of users; and the additional cochlear implant is implanted within a second user included in the plurality of users.

8. The sound processor of claim 1, wherein the detection facility detects the communicative coupling of the sound processor to the cochlear implant by detecting an establishment of a wireless communication link between the sound processor and the cochlear implant.

9. The sound processor of claim 1, wherein the program management facility determines the identifier unique to the cochlear implant by:

querying the cochlear implant; and receiving, in response to the querying of the cochlear implant, data representative of the identifier from the cochlear implant.

10. The sound processor of claim 1, wherein the identifier unique to the cochlear implant comprises a serial number unique to the cochlear implant.

11. The sound processor of claim 1, wherein the program management facility operates in accordance with the identified sound processing program by processing an audio signal in accordance with the identified sound processing program.

12. The sound processor of claim 1, wherein the sound processor comprises a behind-the-ear ("BTE") sound processor.

13. A system comprising:

a sound processor that maintains, within a first memory slot corresponding to a first program switch position, data representative of a first set of sound processing programs associated with the first memory slot and with a plurality of cochlear implants implanted within a plurality of users, and maintains, within a second memory slot corresponding to a second program switch position, data representative of a second set of sound processing programs associated with the second memory slot and with the plurality of cochlear implants implanted within the plurality of users; and a fitting system configured to selectively and communicatively couple to the sound processor;

wherein the fitting system provides the data representative of the first set of sound processing programs and the data representative of the second set of sound processing programs to the sound processor while the fitting system is communicatively coupled to the sound processor.

14. The system of claim 13, wherein the fitting system provides the data representative of the first set of sound processing programs and the data representative of the second set of sound processing programs to the sound processor by:

receiving the data representative of the first set of sound processing programs and the data representative of the second set of sound processing programs directly from a plurality of sound processors associated with the plurality of users;

storing the received data representative of the first set of sound processing programs and the data representative of the second set of sound processing programs;

detecting a communicative coupling of the sound processor to the fitting system; and transmitting, while the sound processor is communicatively coupled to the fitting system, the stored data representative of the first set of sound processing programs and the stored data representative of the second set of sound processing programs to the sound processor.

15. The system of claim 14, wherein the fitting system further:

detects a communicative coupling of an additional sound processor to the fitting system, the additional sound processor not included in the plurality of sound processors;

receives, from the additional sound processor in response to the communicative coupling of the additional sound processor to the fitting system, data representative of a first sound processing program associated with the first memory slot and data representative of a second sound processing program associated with the second memory slot;

includes the data representative of the first sound processing program in the stored data representative of the first set of sound processing programs; and includes the data representative of the second sound processing program in the stored data representative of the second set of sound processing programs.

16. A method comprising:

maintaining, by a sound processor within a first memory slot corresponding to a first program switch position, data representative of a first set of sound processing programs associated with the first memory slot and with a plurality of cochlear implants implanted within a plurality of users;

maintaining, by the sound processor within a second memory slot corresponding to a second program switch position, data representative of a second set of sound processing programs associated with the second memory slot and with the plurality of cochlear implants implanted within the plurality of users;

detecting, by the sound processor, a communicative coupling of the sound processor to a cochlear implant included in the plurality of cochlear implants; and in response to the communicative coupling,
determining, by the sound processor, an identifier unique to the cochlear implant,
determining, by the sound processor, that a program switch associated with the sound processor is in the first program switch position,
querying, by the sound processor in accordance with the determination that the program switch is in the first program switch position, the first set of sound processing programs to identify a sound processing program included in the first set of sound processing programs that is associated with the determined identifier, and
operating, by the sound processor, in accordance with the identified sound processing program.

17. The method of claim 16, further comprising:

determining, by the sound processor, that the program switch switches to being in the second program switch position;

querying, by the sound processor in response to the program switch switching to being in the second program switch position, the second set of sound processing programs to identify a sound processing program included in the second set of sound processing programs that is associated with the determined identifier; and operating, by the sound processor, in accordance with the identified sound processing program included in the second set of sound processing programs.

18. The method of claim 16, further comprising:

detecting, by the sound processor, that the sound processor is uncoupled from the cochlear implant and communicatively couples to an additional cochlear implant included in the plurality of cochlear implants; and in response to the communicative coupling to the additional cochlear implant,
determining, by the sound processor, an additional identifier unique to the additional cochlear implant,
determining, by the sound processor, that the program switch associated with the sound processor is in the first program switch position,
querying, by the sound processor in accordance with the determination that the program switch is in the first program switch position, the first set of sound processing programs to identify an additional sound processing program included in the first set of sound processing programs that is associated with the determined additional identifier, and
operating, by the sound processor, in accordance with the identified additional sound processing program.

19. The method of claim 16, wherein the determining of the identifier unique to the cochlear implant comprises:

querying the cochlear implant; and receiving, in response to the querying of the cochlear implant, data representative of the identifier from the cochlear implant.

20. The method of claim 16, wherein the identifier unique to the cochlear implant comprises a serial number unique to the cochlear implant.

* * * * *